(12) United States Patent
Kim

(10) Patent No.: US 8,357,521 B2
(45) Date of Patent: Jan. 22, 2013

(54) METHOD FOR PRODUCING A BIOBUTANOL USING A THIOLASE WITH IMPROVED ACTIVITY

(75) Inventor: Kyung Jin Kim, Pohang-si (KR)

(73) Assignee: Postech Academy-Industry Foundation, Pohang (KR)

( * ) Notice: Subject to any disclaimer, the term of this patent is extended or adjusted under 35 U.S.C. 154(b) by 0 days.

(21) Appl. No.: 13/253,405

(22) Filed: Oct. 5, 2011

(65) Prior Publication Data

US 2012/0088281 A1     Apr. 12, 2012

(30) Foreign Application Priority Data

Oct. 11, 2010   (KR) .................. 10-2010-0098847

(51) Int. Cl.
    *C12P 7/16*   (2006.01)
(52) U.S. Cl. ........................................ 435/160
(58) Field of Classification Search ............... None
    See application file for complete search history.

(56) References Cited

U.S. PATENT DOCUMENTS

| | | | | |
|---|---|---|---|---|
| 4,424,275 A | * | 1/1984 | Levy ............................ | 435/160 |
| 2008/0311640 A1 | * | 12/2008 | Cox et al. ....................... | 435/168 |
| 2010/0151544 A1 | * | 6/2010 | Papoutsakis et al. ......... | 435/160 |

FOREIGN PATENT DOCUMENTS

WO    WO 2008/072921 A1 *  6/2008

OTHER PUBLICATIONS

Atsumi et al., Metabolic Engineer. 10:305-311, 2008.*
TrEMBL Database Accession No. B3HAI0_ECOLX, May 2009, 1 page.*
UnitProt Accession No. P07097, Aug. 2010, 4 pages.*
Welch et al., Arch. Biochem. Biophys. 273:309-318, 1989.*
Rao et al., Ann. NY Acad. Sci. 506:76-83, 1987.*
Sim et al., Bioresource Technol. 99:2724-2735, 2008.*
Kathleen P. Stim-Herndon et al., "Characterization of an acetyl-CoA C-acetyltransferase (thiolase) gene from *Clostridium acetobutylicum* ATCC 824", Gene, Elsevier Science, vol. 154, 1995, pp. 81-85.
Sang Yup Lee et al., "Fermentative Butanol Production by Clostridia", Biotechnology and Bioengineering, vol. 101, No. 2, 2008, pp. 209-228.
Yan-Ning Zheng et al., "Problems with the microbial production of butanol", J. Ind. Microbiol. Biotechnol., vol. 36, 2009, pp. 1127-1138.
European Patent Office, the extended European search report of the corresponding application (European Patent Application No. 11184303.3, Jan. 24, 2012.
Shota Atsumi and James C Liam, "Metabolic engineering for advanced biofuels production from *Escherichia coli*," Current Opinion in Biotechnology 2008, 19:414-419.

* cited by examiner

*Primary Examiner* — David J Steadman
(74) *Attorney, Agent, or Firm* — Lexyoume IP Meister, PLLC.

(57) ABSTRACT

The present invention relates to a modified thiolase protein with an improved activity, a polynucleotide encoding the modified protein, an expression vector including the polynucleotide, and a transformant, to a composition for producing a biobutanol including the thiolase with an improved activity or a cell expressing the thiolase, and to a method of producing the biobutanol.

1 Claim, 4 Drawing Sheets
(3 of 4 Drawing Sheet(s) Filed in Color)

[Fig.5]

CaTHL (NP_349476)   SEQ ID NO: 1

| | |
|---|---|
| 1 | mkevviasav rtaigsygks lkdvpavdlg ataikeavkk agikpedvne vilgnvlqag |
| 61 | lgqnparqas fkaglpveip amtinkvcgs glrtvslaaq iikagdadvi iaggmenmsr |
| 121 | apylannarw gyrmgnakfv demitdglwd afndyhmgit aeniaerwni sreeqdefal |
| 181 | asqkkaeeai ksgqfkdeiv pvvikgrkge tvvdtdehpr fgstieglak lkpafkkdgt |
| 241 | vtagnasgln dcaavlvims aekakelgvk plakivsygs agvdpaimgy gpfyatkaai |
| 301 | ekagwtvdel dliesneafa aqslavakdl kfdmnkvnvn ggaialghpi gasgarilvt |
| 361 | lvhamqkrda kkglatlcig ggqgtaille kc |

Modified CaTHL (N153Y/A286K)   SEQ ID NO: 2

| | |
|---|---|
| 1 | mkevviasav rtaigsygks lkdvpavdlg ataikeavkk agikpedvne vilgnvlqag |
| 61 | lgqnparqas fkaglpveip amtinkvcgs glrtvslaaq iikagdadvi iaggmenmsr |
| 121 | apylannarw gyrmgnakfv demitdglwd afydyhmgit aeniaerwni sreeqdefal |
| 181 | asqkkaeeai ksgqfkdeiv pvvikgrkge tvvdtdehpr fgstieglak lkpafkkdgt |
| 241 | vtagnasgln dcaavlvims aekakelgvk plakivsygs agvdpkimgy gpfyatkaai |
| 301 | ekagwtvdel dliesneafa aqslavakdl kfdmnkvnvn ggaialghpi gasgarilvt |
| 361 | lvhamqkrda kkglatlcig ggqgtaille kc |

Modified CaTHL (V77Q/N153Y/A286K)   SEQ ID NO: 3

| | |
|---|---|
| 1 | mkevviasav rtaigsygks lkdvpavdlg ataikeavkk agikpedvne vilgnvlqag |
| 61 | lgqnparqas fkaglpqeip amtinkvcgs glrtvslaaq iikagdadvi iaggmenmsr |
| 121 | apylannarw gyrmgnakfv demitdglwd afydyhmgit aeniaerwni sreeqdefal |
| 181 | asqkkaeeai ksgqfkdeiv pvvikgrkge tvvdtdehpr fgstieglak lkpafkkdgt |
| 241 | vtagnasgln dcaavlvims aekakelgvk plakivsygs agvdpkimgy gpfyatkaai |
| 301 | ekagwtvdel dliesneafa aqslavakdl kfdmnkvnvn ggaialghpi gasgarilvt |
| 361 | lvhamqkrda kkglatlcig ggqgtaille kc |

EcTHL (ZP_03027833) SEQ ID NO: 4

| | |
|---|---|
| 1 | mkdvvivgal rtpigcfrga laghsavelg slvvkalier tgvpayavde vilgqvltag |
| 61 | agqnparqsa ikgglpnsvs aitindvcgs glkalhlatq aiqcgeadiv iaggqenmsr |
| 121 | aphvltdsrt gaqlgnsqlv dslvhdglwd afndyhigvt aenlareygi srqlqdayal |
| 181 | ssqqkaraai dagrfkdeiv pvmiqsngqt lvvdtdeqpr tdasaeglar lnpsfdslgs |
| 241 | vtagnassin dgaaavmmms eakaralnlp vlarirafas vgvdpalmgi apvyatrrcl |
| 301 | ervgwqladv dlieaneafa aqalsvgkml ewderrvnvn ggaialghpi gasgcrilvs |
| 361 | lvhemvkma rkglatlcig ggqgvaltie rde |

_US 8,357,521 B2_

SEQUENCE LISTING

<160> NUMBER OF SEQ ID NOS: 18

<210> SEQ ID NO 1
<211> LENGTH: 392
<212> TYPE: PRT
<213> ORGANISM: Artificial Sequence
<220> FEATURE:
<223> OTHER INFORMATION: Amino acid sequence of wild-type CaTHL protein

<400> SEQUENCE: 1

```
Met Lys Glu Val Val Ile Ala Ser Ala Val Arg Thr Ala Ile Gly Ser
  1               5                  10                  15

Tyr Gly Lys Ser Leu Lys Asp Val Pro Ala Val Asp Leu Gly Ala Thr
                 20                  25                  30

Ala Ile Lys Glu Ala Val Lys Lys Ala Gly Ile Lys Pro Glu Asp Val
             35                  40                  45

Asn Glu Val Ile Leu Gly Asn Val Leu Gln Ala Gly Leu Gly Gln Asn
         50                  55                  60

Pro Ala Arg Gln Ala Ser Phe Lys Ala Gly Leu Pro Val Glu Ile Pro
 65                  70                  75                  80

Ala Met Thr Ile Asn Lys Val Cys Gly Ser Gly Leu Arg Thr Val Ser
                 85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350
```

```
Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gln Gly
370                 375                 380

Thr Ala Ile Leu Leu Glu Lys Cys
385                 390

<210> SEQ ID NO 2
<211> LENGTH: 392
<212> TYPE: PRT
<213> ORGANISM: Artificial Sequence
<220> FEATURE:
<223> OTHER INFORMATION: Amino acid sequence of modified CaTHL protein
      (N153Y and A286K)

<400> SEQUENCE: 2

Met Lys Glu Val Val Ile Ala Ser Ala Val Arg Thr Ala Ile Gly Ser
 1               5                  10                  15

Tyr Gly Lys Ser Leu Lys Asp Val Pro Ala Val Asp Leu Gly Ala Thr
                20                  25                  30

Ala Ile Lys Glu Ala Val Lys Lys Ala Gly Ile Lys Pro Glu Asp Val
            35                  40                  45

Asn Glu Val Ile Leu Gly Asn Val Leu Gln Ala Gly Leu Gly Gln Asn
        50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Tyr Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Lys Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320
```

```
Ala Gln Ser Leu Ala Val Ala Lys Asp Leu Lys Phe Asp Met Asn Lys
            325                 330                 335

Val Asn Val Asn Gly Gly Ala Ile Ala Leu Gly His Pro Ile Gly Ala
        340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gln Gly
        370                 375                 380

Thr Ala Ile Leu Leu Glu Lys Cys
385                 390

<210> SEQ ID NO 3
<211> LENGTH: 392
<212> TYPE: PRT
<213> ORGANISM: Artificial Sequence
<220> FEATURE:
<223> OTHER INFORMATION: Amino acid sequence of modified CaTHL protein
      (V77Q, N153Y and A286K)

<400> SEQUENCE: 3

Met Lys Glu Val Val Ile Ala Ser Ala Val Arg Thr Ala Ile Gly Ser
  1               5                  10                  15

Tyr Gly Lys Ser Leu Lys Asp Val Pro Ala Val Asp Leu Gly Ala Thr
             20                  25                  30

Ala Ile Lys Glu Ala Val Lys Lys Ala Gly Ile Lys Pro Glu Asp Val
         35                  40                  45

Asn Glu Val Ile Leu Gly Asn Val Leu Gln Ala Gly Leu Gly Gln Asn
     50                  55                  60

Pro Ala Arg Gln Ala Ser Phe Lys Ala Gly Leu Pro Gln Glu Ile Pro
 65                  70                  75                  80

Ala Met Thr Ile Asn Lys Val Cys Gly Ser Gly Leu Arg Thr Val Ser
                 85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
        130                 135                 140

Thr Asp Gly Leu Trp Asp Ala Phe Tyr Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Ile Lys Gly Arg Lys
        195                 200                 205

Gly Glu Thr Val Val Asp Thr Asp Glu His Pro Arg Phe Gly Ser Thr
        210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Lys Ile Met
        275                 280                 285
```

```
Gly Tyr Gly Pro Phe Tyr Ala Thr Lys Ala Ala Ile Glu Lys Ala Gly
        290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
            325                 330                 335

Val Asn Val Asn Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
        370                 375                 380

Thr Ala Ile Leu Leu Glu Lys Cys
385                 390

<210> SEQ ID NO 4
<211> LENGTH: 393
<212> TYPE: PRT
<213> ORGANISM: Artificial Sequence
<220> FEATURE:
<223> OTHER INFORMATION: Amino acid sequence of wild-type EcTHL protein

<400> SEQUENCE: 4

Met Lys Asp Val Val Ile Val Gly Ala Leu Arg Thr Pro Ile Gly Cys
1               5                   10                  15

Phe Arg Gly Ala Leu Ala Gly His Ser Ala Val Glu Leu Gly Ser Leu
            20                  25                  30

Val Val Lys Ala Leu Ile Glu Arg Thr Gly Val Pro Ala Tyr Ala Val
        35                  40                  45

Asp Glu Val Ile Leu Gly Gln Val Leu Thr Ala Gly Ala Gly Gln Asn
    50                  55                  60

Pro Ala Arg Gln Ser Ala Ile Lys Gly Gly Leu Pro Asn Ser Val Ser
65                  70                  75                  80

Ala Ile Thr Ile Asn Asp Val Cys Gly Ser Gly Leu Lys Ala Leu His
                85                  90                  95

Leu Ala Thr Gln Ala Ile Gln Cys Gly Glu Ala Asp Ile Val Ile Ala
            100                 105                 110

Gly Gly Gln Glu Asn Met Ser Arg Ala Pro His Val Leu Thr Asp Ser
        115                 120                 125

Arg Thr Gly Ala Gln Leu Gly Asn Ser Gln Leu Val Asp Ser Leu Val
    130                 135                 140

His Asp Gly Leu Trp Asp Ala Phe Asn Asp Tyr His Ile Gly Val Thr
145                 150                 155                 160

Ala Glu Asn Leu Ala Arg Glu Tyr Gly Ile Ser Arg Gln Leu Gln Asp
                165                 170                 175

Ala Tyr Ala Leu Ser Ser Gln Gln Lys Ala Arg Ala Ala Ile Asp Ala
            180                 185                 190

Gly Arg Phe Lys Asp Glu Ile Val Pro Val Met Ile Gln Ser Asn Gly
        195                 200                 205

Gln Thr Leu Val Val Asp Thr Asp Glu Gln Pro Arg Thr Asp Ala Ser
    210                 215                 220

Ala Glu Gly Leu Ala Arg Leu Asn Pro Ser Phe Asp Ser Leu Gly Ser
225                 230                 235                 240

Val Thr Ala Gly Asn Ala Ser Ser Ile Asn Asp Gly Ala Ala Ala Val
                245                 250                 255

Met Met Met Ser Glu Ala Lys Ala Arg Ala Leu Asn Leu Pro Val Leu
```

```
                        260                 265                 270
Ala Arg Ile Arg Ala Phe Ala Ser Val Gly Val Asp Pro Ala Leu Met
                275                 280                 285

Gly Ile Ala Pro Val Tyr Ala Thr Arg Arg Cys Leu Glu Arg Val Gly
            290                 295                 300

Trp Gln Leu Ala Asp Val Asp Leu Ile Glu Ala Asn Glu Ala Phe Ala
305                 310                 315                 320

Ala Gln Ala Leu Ser Val Gly Lys Met Leu Glu Trp Asp Glu Arg Arg
                325                 330                 335

Val Asn Val Asn Gly Gly Ala Ile Ala Leu Gly His Pro Ile Gly Ala
            340                 345                 350

Ser Gly Cys Arg Ile Leu Val Ser Leu Val His Glu Met Val Lys Arg
                355                 360                 365

Asn Ala Arg Lys Gly Leu Ala Thr Leu Cys Ile Gly Gly Gly Gln Gly
            370                 375                 380

Val Ala Leu Thr Ile Glu Arg Asp Glu
385                 390

<210> SEQ ID NO 5
<211> LENGTH: 34
<212> TYPE: DNA
<213> ORGANISM: Artificial Sequence
<220> FEATURE:
<223> OTHER INFORMATION: CaTHL NdeI Forward primer

<400> SEQUENCE: 5
gcgcgcatat gaaagaagtt gtaatagcta gtgc                              34

<210> SEQ ID NO 6
<211> LENGTH: 37
<212> TYPE: DNA
<213> ORGANISM: Artificial Sequence
<220> FEATURE:
<223> OTHER INFORMATION: CaTHL XhoI Reverse primer

<400> SEQUENCE: 6
gcgcgctcga ggcactttc tagcaatatt gctgttc                            37

<210> SEQ ID NO 7
<211> LENGTH: 38
<212> TYPE: DNA
<213> ORGANISM: Artificial Sequence
<220> FEATURE:
<223> OTHER INFORMATION: CaTHL V77Q Forward primer

<400> SEQUENCE: 7
cttttaaagc aggattacca caagaaattc cagctatg                          38

<210> SEQ ID NO 8
<211> LENGTH: 38
<212> TYPE: DNA
<213> ORGANISM: Artificial Sequence
<220> FEATURE:
<223> OTHER INFORMATION: CaTHL V77Q Reverse primer

<400> SEQUENCE: 8
catagctgga atttcttgtg gtaatcctgc tttaaaag                          38

<210> SEQ ID NO 9
<211> LENGTH: 38
<212> TYPE: DNA
<213> ORGANISM: Artificial Sequence
<220> FEATURE:
```

<223> OTHER INFORMATION: CaTHL P80T(+V77Q) Forward primer

<400> SEQUENCE: 9
gattaccaca agaaattaca gctatgacta ttaataag                38

<210> SEQ ID NO 10
<211> LENGTH: 38
<212> TYPE: DNA
<213> ORGANISM: Artificial Sequence
<220> FEATURE:
<223> OTHER INFORMATION: CaTHL P80T(+V77Q) Reverse primer

<400> SEQUENCE: 10
cttattaata gtcatagctg taatttcttg tggtaatc                38

<210> SEQ ID NO 11
<211> LENGTH: 33
<212> TYPE: DNA
<213> ORGANISM: Artificial Sequence
<220> FEATURE:
<223> OTHER INFORMATION: CaTHL N153Y Forward primer

<400> SEQUENCE: 11
gattgtggga tgcattttat gattaccaca tgg                33

<210> SEQ ID NO 12
<211> LENGTH: 33
<212> TYPE: DNA
<213> ORGANISM: Artificial Sequence
<220> FEATURE:
<223> OTHER INFORMATION: CaTHL N153Y Reverse primer

<400> SEQUENCE: 12
ccatgtggta atcataaaat gcatcccaca atc                33

<210> SEQ ID NO 13
<211> LENGTH: 31
<212> TYPE: DNA
<213> ORGANISM: Artificial Sequence
<220> FEATURE:
<223> OTHER INFORMATION: CaTHL A286K Forward primer

<400> SEQUENCE: 13
caggagttga cccaaaaata atgggatatg g                31

<210> SEQ ID NO 14
<211> LENGTH: 31
<212> TYPE: DNA
<213> ORGANISM: Artificial Sequence
<220> FEATURE:
<223> OTHER INFORMATION: CaTHL A286K Reverse primer

<400> SEQUENCE: 14
ccatatccca ttattttggg gtcaactcct g                31

<210> SEQ ID NO 15
<211> LENGTH: 33
<212> TYPE: DNA
<213> ORGANISM: Artificial Sequence
<220> FEATURE:
<223> OTHER INFORMATION: CaTHL Y290T(+A286K) Forward primer

<400> SEQUENCE: 15
cccaaaaata atgggaactg gacctttcta tgc                33

<210> SEQ ID NO 16

```
<211> LENGTH: 33
<212> TYPE: DNA
<213> ORGANISM: Artificial Sequence
<220> FEATURE:
<223> OTHER INFORMATION: CaTHL Y290T(+A286K) Reverse primer

<400> SEQUENCE: 16
gcatagaaag gtccagttcc cattattttt ggg                                33

<210> SEQ ID NO 17
<211> LENGTH: 34
<212> TYPE: DNA
<213> ORGANISM: Artificial Sequence
<220> FEATURE:
<223> OTHER INFORMATION: EcTHL_F_BamHI primer

<400> SEQUENCE: 17
ccggatccat gaaaaattgt gtcatcgtca gtgc                               34

<210> SEQ ID NO 18
<211> LENGTH: 34
<212> TYPE: DNA
<213> ORGANISM: Artificial Sequence
<220> FEATURE:
<223> OTHER INFORMATION: EcTHL_F_XhoI primer

<400> SEQUENCE: 18
ccctcgagtt aattcaaccg ttcaatcacc atcg                               34
```

METHOD FOR PRODUCING A BIOBUTANOL USING A THIOLASE WITH IMPROVED ACTIVITY

CROSS-REFERENCE TO RELATED APPLICATION

This application claims priority to and the benefit of Korean Patent Application No. 10-2010-0098847 filed in the Korean Intellectual Property Office on Oct. 11, 2010, and the entire contents of which are incorporated herein by reference.

BACKGROUND OF THE INVENTION (a) Field of the Invention

The present invention relates to a modified thiolase protein with an improved activity, a polynucleotide encoding the modified protein, an expression vector and a transformant including the polynucleotide, a composition for producing biobutanol including the modified thiolase with an improved activity or a cell expressing the modified thiolase, and a method of producing biobutanol.

(b) Description of the Related Art

The increased dependence on the fossil fuel causes various problems such as global warming and high oil price. To resolve the problems, there are many researches to develop an alternative energy. The bioenergy has advantage of sufficient energy source and only an alternative energy source of fuel energy for vehicle, and has been researched widely. Until now, most researches on the bioenergy concentrates to production of bioethanol, but recently, research on more excellent biobutanol than bioethanol is performed actively. Biobutanol has high energy content, and can be easily transportation and storage, and directly used as a fuel energy for vehicle.

The biobutanol has been known to be produced by anaerobic bacteria, _Clostridium acetobutylicum_ at most efficiently. Biobutanol is synthesized from acetyl-CoA through complicated six steps where each step is performed by each different protein. However, there is no research on the protein structure analysis of enzymes involved in the synthesis of biobutanol, thereby not identifying the synthesis of biobutanol at the molecular level.

Therefore, there is still need for identifying the mechanism of biotutanol synthesis at the molecular level by the structural analysis of relevant proteins, and for developing the modified protein due to information of protein structure.

SUMMARY OF THE INVENTION

The present inventors identified the mechanism of proteins related with the production of biobutanol in a molecular level through an analysis of protein structure, and developed the improved modified protein on the basis of information of protein structure, to complete the present invention.

An embodiment of the present invention provides a modified thiolase(acetyl-CoA C-acetyltransferase, THL) protein with improved activity.

Another embodiment provides a gene encoding the modified protein of thiolase.

Further embodiment provides an expression vector and a transformant including a gene encoding the modified protein of thiolase.

Still other embodiment provides a method of producing biobutanol using the modified thiolase protein or the transformant.

Further embodiment provides a method of controlling an activity of thiolase derived from _Clostridium acetobutylicum_ via redox-switch modulation.

Other embodiment provides a method of producing biobutanol by using a thiolase of _E. coli_.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 5 is an amino acid sequences of CaTHL (W/T), double-modified protein of CaTHL (N153Y/A286K), triple-modified protein of CaTHL (V77Q/N153Y/A286K), and EcTHL (W/T) where the modified parts of CaTHL (N153Y/A286K) and CaTHL (V77Q/N153Y/A286K) are emphasized in gray shade.

DETAILED DESCRIPTION OF THE EMBODIMENTS

The present inventors identified the three dimensional structure of acetyl-CoA acetyltransferase (thiolase, THL) related with biobutanol biosynthesis by performing mass production of THL protein and the crystallization, and investigated the regulation mechanism of THL protein at molecular level using information on the three dimensional structure of protein. In addition, the present inventors developed a modified protein having the activity 2.5 times higher than the known THL by modifying the regulation mechanism of THL protein using the gene modification technique, and completed the present invention.

Thus, an embodiment of the present invention provides a modified protein of thiolase (Ca THL) derived from _Clostridium acetobutylicum_ having increased activity. The thiolase derived from _Clostridium acetobutylicum_ has an amino acid sequence of SEQ ID NO: 1 (Accession No. NP_349476, 392aa), and the modified protein of thiolase includes two following mutations of amino acid:

substitution of asparagine (Asn) at $153^{rd}$ position of the amino acid sequence of thiolase as set forth in SEQ ID NO:1 with tyrosine (Tyr) (N153Y); and substitution of alanine (Ala) at $286^{th}$ position of an amino acid sequence of thiolase as set forth in SEQ ID NO:1 with lysine (Lys) or arginine (Arg) (A286K or A286R).

Optionally, the modified thiolase protein may further include at least one modification selected from the followings:

substitution of valine (Val) at 77th position of an amino acid sequence of thiolase as set forth in SEQ ID NO:1 with glutamine (Gln) or glutamate (Glu) (V77Q or V77E);

substitution of proline (Pro) at 80th position of an amino acid sequence of thiolase as set forth in SEQ ID NO:1 with threonine (Thr) or serine (Ser)(P80T or P80S); and substitution of Tyrosine (Tyr) at 290th position of an amino acid sequence of thiolase as set forth in SEQ ID NO:1 with threonine (Thr) or serine (Ser) (Y290T or Y290S).

In an embodiment of the present invention, the examples of modified thiolase protein include the modified protein having modification of two amino acid residues such as N153Y and A286K (SEQ ID NO: 2) or having modification of three amino acid residues such as V77Q, N153Y and A286K (SEQ ID NO: 3) in the amino acid of thiolase derived from Clostridium acetobutylicum.

Figure 2:
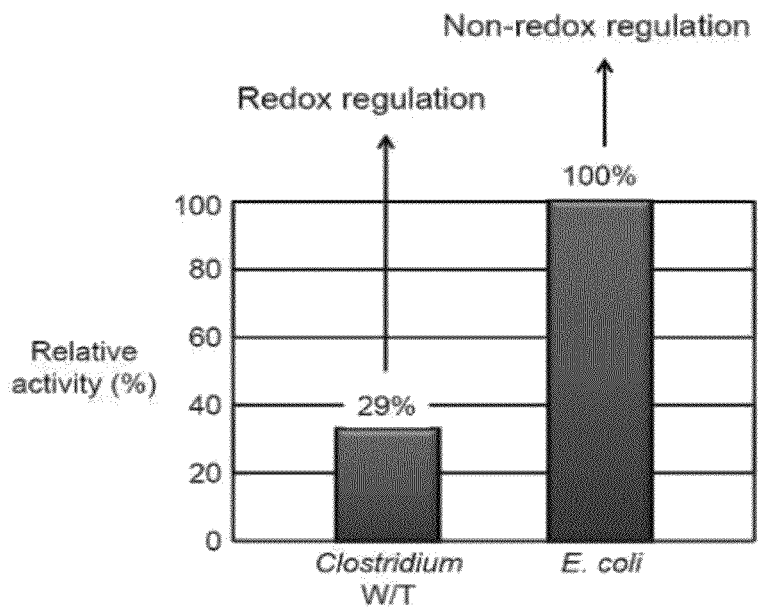
FIG. 2 is a graph showing the protein activities compared _Clostridium acetobutylicum_ THL protein (CaTHL) with _E. coli_ THL protein (EcTHL).

The modified thiolase protein of the present invention has a characteristic of redox-switch modulation that wild-type thiolase derived from Clostridium acetobutylicum is active under the reduction condition, and is inactive under the oxidized condition, and thus overcomes a disadvantage of lower activity than thiolase derived from other microorganism (see FIG. 2). Since the modified thiolase protein has a characteristic of non-redox switch modulation that maintains its activity under the oxidized condition, the modified protein shows notably better activity than wild-type thiolase derived from Clostridium acetobutylicum (see Example 4 and FIG. 4).

As explained hereinafter, the reason to explain that the thiolase derived from Clostridium acetobutylicum gets inactive under the oxidative condition is based on the formation of disulfide bond between the cysteins (C88, C378) under the oxidative condition due to redox-switch modulation. The amino acid residues at positions 77, 80, 153, 286 and 290 of SEQ ID NO: 1 locates around the region of disulfide bond formed between the Cysteines (C88, C378), and the stable hydrogen bond formed the amino acid residues can make the thiolase have higher structural stability. In this case, the distance to form the disulfide bond is not sufficient, and thus, two cysteins may not form the disulfide bond even under the oxidative condition. The amino acid residues which are specifically important to form the stable hydrogen bond being competitive to the disulfide bond are the positions of 153 and 286 of SEQ ID NO:1.

Accordingly, in the case that the amino acids at the positions is substituted with an amino acid being capable of contributing to the strong and stable hydrogen bond, the substitution can contribute the structural stability of thiolase and prevent the formation of disulfide bond even under the oxidative condition, thereby maintaining the activity of thiolase.

To form more stable and strong hydrogen bond, for example, Asparagine (Asn) at position 153 of an amino acid sequence as set forth in SEQ ID NO: 1 can substituted with Tyrosine (Tyr) (N153Y); and Alanine (Ala) at position 286 of an amino acid sequence as set forth in SEQ ID NO: 1 can be substituted with Lysine (Lys) or Arginine (Arg) A286K or A286R).

Beside the substitutions of amino acid, the modified protein comprising at least one modification selected from the group consisting of: a substitution of Valine (Val) at position 77 of an amino acid sequence as set forth in SEQ ID NO: 1 with glutamine (Gln) or glutamate (Glu) (V77Q or V77E); a substitution of proline (Pro) at position 80 of an amino acid sequence as set forth in SEQ ID NO: 1 with Threonine (Thr) or Serine (Ser) (P80T or P80S); and a substitution of Tyrosine (Tyr) at position 290 of an amino acid sequence as set forth in SEQ ID NO: 1 with Threonine (Thr) or Serine (Ser) (Y290T or Y290S). When the modified protein includes at least one modification additionally, the decreased activity in the oxidative condition can be recovered more effectively.

Because the structural stability around the disulfide bond is in competitive relationship with the disulfide bond (see Example 3), the modification such as substitution of amino acid can make the amino acid residues surrounding the disulfide bond be more stable by forming strong hydrogen bond between the amino acids surrounding the disulfide bond, and thus prevent the formation of disulfide bond even under the oxidative condition due to sufficient accessibility between the Cysteins (C88, C378). Thus, the modified protein derived from the thiolase of Clostridium acetobutylicum which is controlled by non-redox switch modulation can be obtained.

Another embodiment provides a polynucleotide encoding the modified protein derived from the thiolase of Clostridium acetobutylicum, for example the protein having an amino acid sequence of SEQ ID NO: 2 or SEQ ID NO: 3, and an expression vector including the polynucleotide.

Hereinafter, the term, "expression vector" refers to a plasmid, a virus or other transferring vehicle that has a cloned polynucleotide encoding the modified protein of thiolase. The polynucleotide cloned according to the present invention can include an expression-controlling sequence to be operably linked, the polynucleotide and regulatory nucleotide can be contained in an expression vector including a selective marker and replication origin. The term, "operably linked" means that the polynucleotide is linked to the regulatory nucleotide in a manner of being capable of controlling the polynucleotide by the regulatory nucleotide. The term, "expression-controlling sequence" means a DNA sequence controlling the operably-linked polynucleotide in a specific host. The expression-controlling sequence includes at least one selected from the group consisting of a transcription promoter, an operator for regulating the transcription, a coding sequence for suitable mRNA ribosome binding site, and a terminator for transcription and translation.

Any vector can be used for preparing the expression vector without limitation, and all plasmid, virus or other transferring vehicle used for expressing a gene in a host can be applied for the present invention. The examples of plasmid are the plasmids derived from E. coli (pBR322, pBR325, pUC118, pUC119, and pET-22b(+)), the plasmid derived from B. subtilis (pUB110 and pTP5), the plasmid derived from yeast (YEp13, YEp24 and YCp50) and the like. The examples of virus include animal viruses such as retrovirus, adenovirus, vaccinia virus and the like, and an insect virus such as baculovirus, but not limited thereto.

Another embodiment provides a tramsformant (transformed cell) which is obtained by transforming a host cell with the expression vector.

The host cell can be any prokaryotic cell including a unicellular organism such as a bacteria (for examples, E. coli, Clostridia sp., E. coli and the like), and eukaryotic cell including yeast and etc. The exemplified host can be selected from the group consisting of Clostridia sp. such as Clostridium acetobutylicum, Clostridium beijerinckii, Clostridium saccharoperbutylacetonicum, or Clostridium saccharobutylicum, E. coli and the like, but not limited thereto.

The method of transforming the host can be performed by any method used generally for introducing the polynucleotide sequence encoding the modified protein of thiolase into the host. For example, the methods of transforming include $CaCl_2$ method, heat shock method, particle gun bombardment, Silicon carbide whiskers, sonication, electroporation, and PEG precipitation, but not limited thereto.

Figure 3:
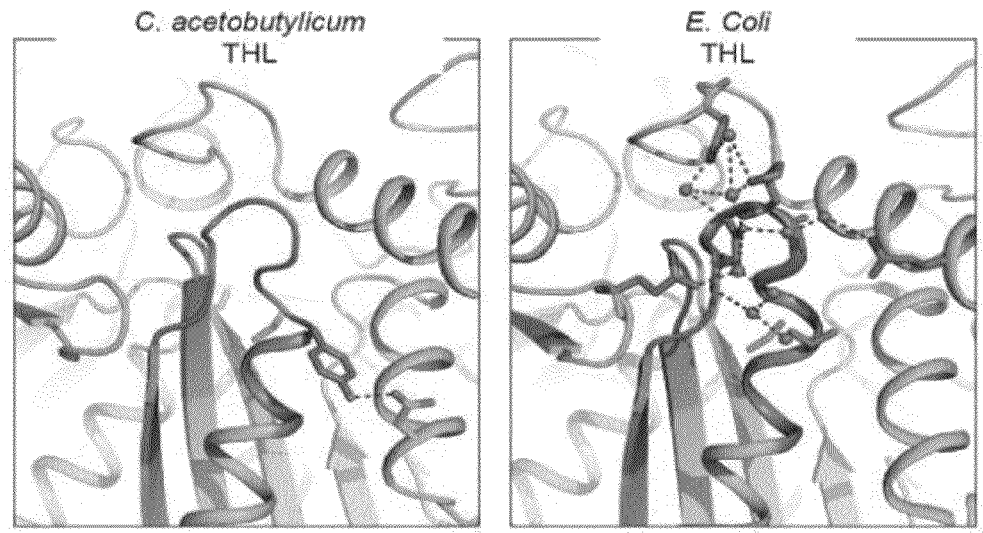
FIG. 3 is a schematic diagram showing the structural stability in the region surrounding the hydrogen bond which is compared _Clostridium acetobutylicum_ THL protein (CaTHL) with _E. coli_ THL protein (EcTHL).

The present inventor found that the thiolase derived from E. coli (EcTHL, ZP_03027833, Ec number=2.3.1.9, SEQ ID NO: 4, 393 aa) had relatively higher activity than that derived from *Clostridium acetobutylicum* (see FIG. 2), According to the present inventors, the thiolase of *Clostridium acetobutylicum* is controlled by redox switch modulation and thus shows decreased activity under the oxidative condition. On the other hand, the activity of thiolase derived from *E. coli* is not decreased, because it has non-redox switch modulation which is not affected by the oxidative condition. The non-redox switch modulation of thiolase derived from *E. coli* was confirmed by the analysis of three dimensional structure (FIG. 3).

Further embodiment provides a use of thiolase derived from *E. coli* for producing biobutanol. Thiolase derived from *E. coli* can be used in a form of *E. coli* cell expressing it, or a transformant of other microorganisms (for examples, *Clostridia* sp. such as *Clostridium acetobutylicum, Clostridium beijerinckii, Clostridium saccharoperbutylacetonicum,* or *Clostridium saccharobutylicum*).

An embodiment provides a composition for producing a biobutanol including at least one selected from the group consisting of a modified protein of thiolase derived from *Clostridium acetobutylicum* with an improved activity, a polynucleotide encoding the modified protein, an expression vector including the polynucleotide, and a transformant; and a modified protein of thiolase (SEQ ID NO: 4) derived from *E. coli,* a polynucleotide encoding the modified protein, an expression vector including the polynucleotide, and a cell expressing the thiolase derived from *E. coli.* The preferred example of the composition can be at least one selected from the group consisting of a transformant expressing modified protein of thiolase derived from *Clostridium acetobutylicum* and a cell expressing the modified protein of thiolase (SEQ ID NO: 4) derived from *E. coli* which can be a transformant expressing the modified protein of thiolase (SEQ ID NO: 4) derived from *E. coli,* or a wild-type *E. coli* expressing the thiolase (SEQ ID NO: 4).

An embodiment of present invention provides a method of producing a biobutanol by using the composition. That is, as the composition used for producing a biobutanol is described above, the composition can be at least one selected from the group consisting of a transformant expressing modified protein of thiolase derived from *Clostridium acetobutylicum* and a cell expressing the modified protein of thiolase (SEQ ID NO: 4) derived from *E. coli* which can be a transformant expressing the modified protein of thiolase (SEQ ID NO: 4) derived from *E. coli,* or a wild-type *E. coli* expressing the thiolase (SEQ ID NO: 4).

More specifically, the method of producing the biobutanol includes the steps of: culturing the composition for producing a biobutanol, with a carbon source, and recovering produced biobutanol.

The carbon source can be any carbon-source containing at least one carbon atom and being used by microorganism and for example, includes monosaccharides such as glucose, fructose, galactose, mannose, xylose, and the like; disaccharides such as lactose, maltose, sucrose, cellobiose and the like; oligosaccharides; polysaccharides such as cellulose, hemicelluloses, starch, xylane and the like; single carbon substrate including only one carbon atom such as methanol; and polyol such as glycerol, but not limited thereto.

A culturing method used generally for the host cell can be applied for the present invention by using all media for suitably culturing the hose cell. The culture condition can be the same as that of used host. For example, the *Clostridia* sp. can be cultured at 0° C. to 55° C., or preferably 25° C. to 40° C. Specifically, *Clostridium acetobutylicum* can be cultured at about 35° C.

In considering that the thiolase derived from *Clostridium acetobutylicum* is activated under the reduction condition, an embodiment of the present invention provides a method of producing the biotutanol including a step of reacting *Clostridium acetobutylicu* under the non-oxidative condition such as reduction condition. The method includes the steps of: culturing *Clostridium acetobutylicum* with a carbon source, and recovering the produced biobutanol.

The non-oxidative condition such as reduction condition cannot be limited particularly, and any reduction condition used in the relevant art can be applied for the method for examples, the reduction condition includes the condition of addition of a reducing agent, such as beta-mercaptoethanol (BME), dithiothreitol (DTT), and the like.

The present invention will be described in more detail.

Figure 1:
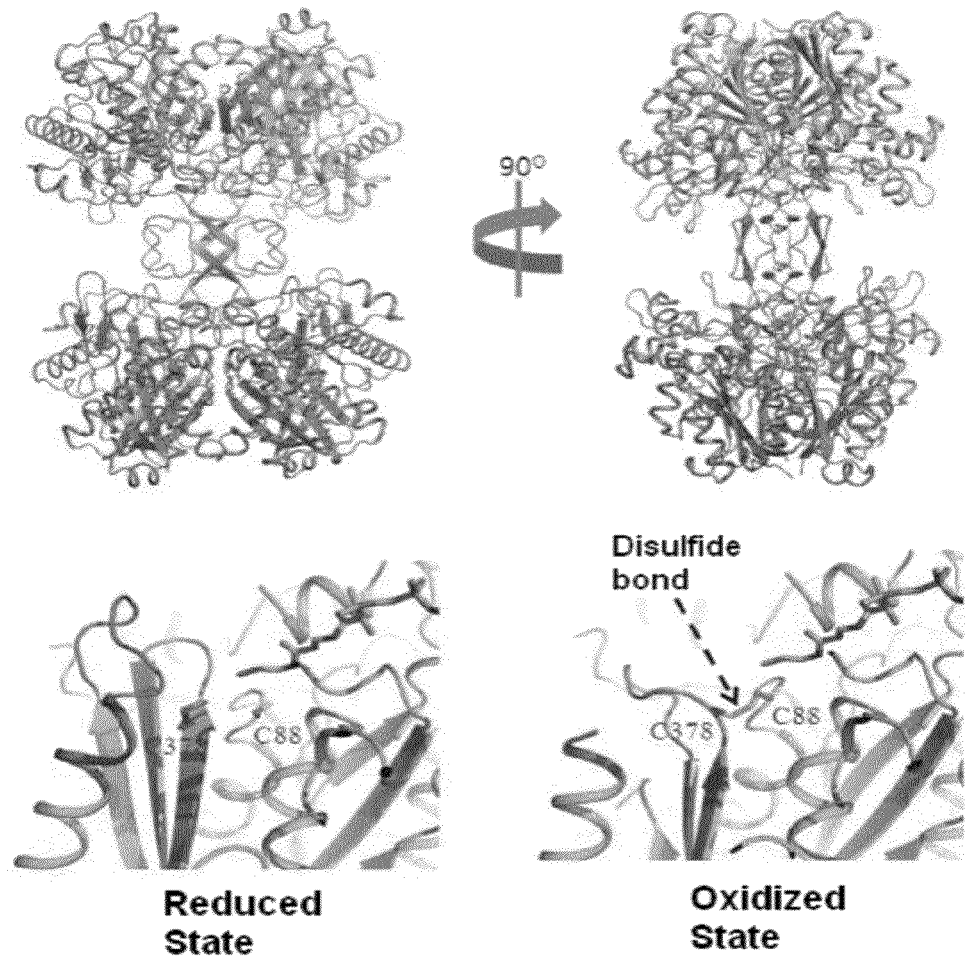
FIG. 1 shows a protein three-dimensional structure (Top part) and a mechanism of redox-switch modulation (Bottom part) of THL protein of _Clostridium acetobutylicumredox_-switch modulation.

The present inventors identified the three dimensional structure of *Clostridium acetobutylicum* THL (CaTHL) which involved in the biosynthesis of biobutanol (FIG. 1). Protein CaTHL catalyzes the reaction of synthesis for acetoacetyl-CoA using two molecules of Acetyl-CoA at first step of biobutanol synthesis. The present inventors found the mechanism of protein by identifying the binding structure of THL and acetyl-CoA and that two Cycteins (C88, C378) are in the active region of the protein and involves in its activity.

As an important point of the present invention is that the protein activity is controlled by redox-switch modulation where the activity is regulated depending on the change of oxidation-reduction condition via the reversible disulfide bond formed between two Cysteins. The two Cysteins are reduced under the reduction condition for the protein to show the activity. However, the Cysteins form the disulfide bond under the oxidative condition and thus cannot involve in the activity of the protein, thereby making the protein be inactive. The reversible disulfide bond which is changed depending on the oxidation/reduction condition accompanies the structural change in the surrounding region. The present inventors found that the structure surrounding the disulfide bond was normal under the reduction condition, but could not be stable under the oxidative condition.

It has been reported that the biotutanol synthesis was controlled sensitively depending on the oxidation/reduction condition. The control of biobutanol synthesis is explained very well and fully supported by the redox-switch modulation of the present invention. That is, the protein shows activity due to the reduction of two Cysteins (C88, C378), and can synthesize the biobutanol. On the other hand, the protein is inactive due to the formation of disulfide bond and thus is not capable of synthesizing biobutanol.

Recently, the ongoing research is related to biobutanol production by using *E. coli* transformed with the gene relating with the biobutanol biosynthesis. In order that the present inventors identify the presence of THL in *E. coli* (EcTHL) and the control mechanism thereof, they studied three dimensional structure and biochemical analysis of the protein. The obtained results (FIGS. 2 and 3) identified that EcTHL did not controlled by the redox-switch modulation, unlike CaTHL.

The redox-switch modulation of CaTHL which has been identified by the present inventors is very unique.

The present inventors measured the effect of the controlling mechanism of CaTHL, and EcTHL on each protein activity. Interestingly, the activity of wild-type CaTHL was about 30% of EcTHL activity (100%) which could not be controlled by redox-switch modulation (FIG. 2). Such result suggests that most CaTHLs are not active due to the formation of disulfide bond under the mild oxidative condition (that is relatively oxidative condition compared to the initial condition).

In fact, the amino acid sequence of CaTHL (NP_349476, Ec number=2.3.1.9, SEQ ID NO: 1) has 60% of homology with that of EcTHL (ZP_03027833, Ec number=2.3.1.9, SEQ ID NO: 4) and very similar structure as a whole.

The present inventors researched that only CaTHL derived from *Clostridium acetobutylicum* has a redox-switch modulation in spite of the similarities on amino acid sequence and whole structure of CaTHL and EcTHL. It has been known that *Clostridium acetobutrylicum* is an anaerobic bacteria but *E. coli* is an aerobic bacteria, and that the cytosol of anaerobic bacteria maintains relative reduction state. The physiological difference between *E. coli* and *Clostridium acetobutrylicum* seems to partly explain the cause of the different redox-switch modulation.

However, the reason of different redox-switch modulation at the molecular structure level was identified by the analysis of three dimensional structure for three kinds of proteins. As described above, two Cysteins of CaTHL form the disulfide bond under the oxidative condition, thereby inducing the structural change the region surrounding them. As a result of specific analysis for three kinds of proteins, they had a large difference in the structural stability in the surrounding region inducing the structural change (FIG. 3). The surrounding region of EcTHL was stable due to the strong hydrogen bond, but that of CaTHL was not stable and had no hydrogen bond.

According to the present invention, the stability in the region surrounding two Cysteins has a competitive structural relationship with the formation of disulfide bond. That is, the binding force of disulfide bond in CaTHL is very strong, compared to the stability of the surrounding region, and thus can form the disulfide bond under the oxidative condition. EcTHL shows high stability in the surround region, and the disulfide bond does not have sufficient force to induce the structural change in the surrounding region. Thus, it is not possible to form disulfide bond in EcTHL.

The present inventors identified for the first time that the different controlling mechanism of two proteins having similar structure and function was caused by the structural stability of protein.

In putting the results together, CaTHL showed a low activity due to redox-switch modulation and the decreased biobutanol synthesis by being inactivated under the relatively oxidative condition. On the other hand, EcTHL represented high efficiency of biobutanol synthesis due to high structural stability.

Unlike EcTHL, the redox-switch modulation of CaTHL is caused by low structural stability in the region surrounding the disulfide bond. Such important properties of CaTHL can make the development of modified protein with high activity by modifying the modulation mechanism. The present inventors made the amino acid residues in surrounding region form the strong hydrogen bond by modifying the amino acid residues surrounding the active site of CaTHL with employing the site-directed point mutagenesis, and developed the modified CaTHL protein with non-redox switch modulation. The CaTHL modified protein of the present invention may be any protein which has at least one modification among V77Q, N153Y, and A286K of SEQ ID NO: 1, for examples, a double-modified protein of N153Y/A286K, and triple-modified protein of V77Q/N153Y/A286K.

The biochemical method confirmed that the disulfide bond was not formed even under the oxidative condition (Example 4). The result of the comparison test of activity (upper part of FIG. 4) confirmed that CaTHL modified protein having non-redox switch modulation showed about 2.5 times increased activity than that of wild-type CaTHL. In particular, the 3D structure of the modified protein including a substitution of Asparagin (Asn) at position 153 of an amino acid sequence as set forth in SEQ ID NO: 1 with Tyrosine (Tyr) (N153Y); and a substitution of Alanine (Ala) at position 286 of an amino acid sequence as set forth in SEQ ID NO: 1 with Lysine (Lys) or Arginine (Arg) (A286K or A286R) was identified to prove stable hydrogen bond in the surrounding region and no disulfide formation between two Cysteins (C88, C378) (bottom part of FIG. 4).

Figure 4:
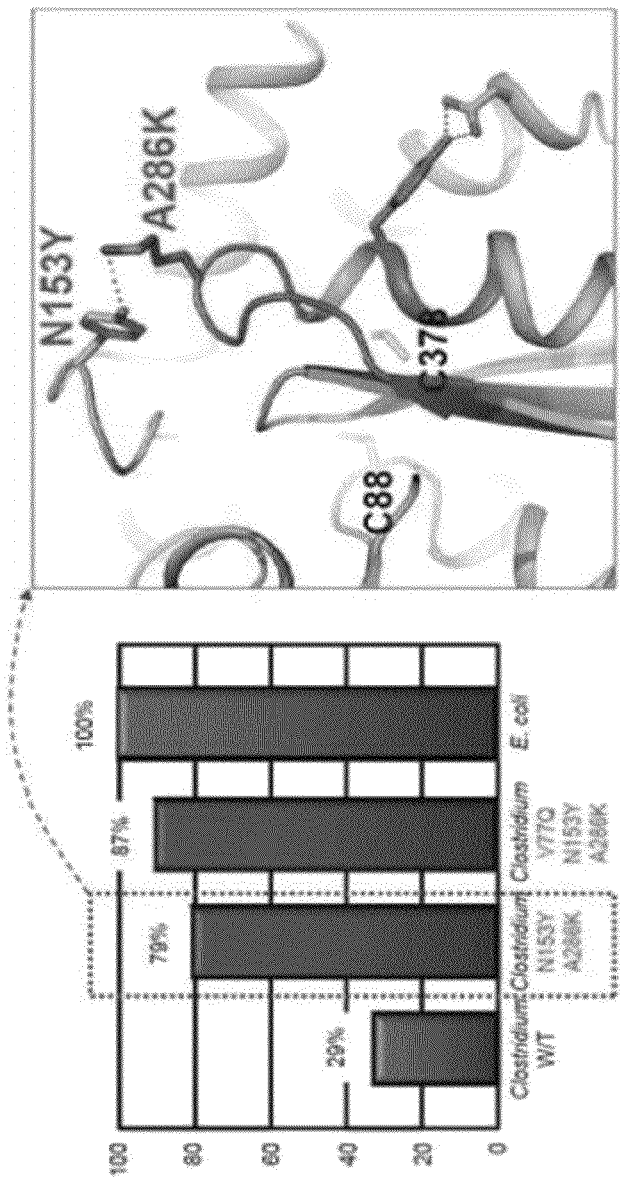
FIG. 4 is a three-dimensional structure of double-modified protein of CaTHL (N153Y/A286K), and a graph of comparison on the activities of CaTHL (W/T), double-modified protein of CaTHL (N153Y/A286K), triple-modified protein of CaTHL (V77Q/N153Y/A286K), and EcTHL (W/T).

In addition, even though the structural change was not introduced into EcTHL, it represented high efficiency of biobutanol synthesis due to the structural stability (FIGS. 2 and 4).

In considering that the protein with high functionality is developed by the modification of the activity-controlling mechanism of CaTHL, an essential protein related with the biobutanol synthesis causes, there is an important meaning and promising effect in two important aspects. One aspect provides a technique of structure-based redox-swapping. For the first time, the present invention provides the modification of the protein having a redox-switch modulation into the protein having non-redox switch modulation. Until now, it has been reported that various proteins have redox-switch modulation using the disulfide bond. However, there is no report for modifying the redox-switch modulation by understanding the structure at a molecular biological level. Thus, the present inventors developed new technique of molecular engineering which is named as structure-based protein engineering, redox-swapping, or structure-based redox-swapping.

The new technique of molecular engineering can be developed by analyzing the structural property of the modulation mechanism on the basis of the identification of the 3D structure, and introducing the site-directed point mutagenesis, but cannot be achieved by random mutation with no information on the protein structure. The technique of the present invention can be applied to other proteins as well as CaTHL and thus can be widely used for developing new modified protein with high functionality.

The other aspect is to produce the biobutanol at high efficiency. As described above, Modified CaTHL protein having non-redox switch modulation represented higher efficiency at about 2.5 times, compared to wild-type CaTHL protein. By introducing the modified gene of CaTHL into *Clostridium acetybutylicum* and replacing the wild-type CaTHL gene, it is possible to induce the biobutanol synthesis under the relatively-oxidative condition. Such trials are expected to be directly used for improvement in the biobutanol productivity. Though the biobutanol has an excellent property as an alternative fuel for vehicle rather than bioethanol, it can be used limitedly due to its lower productivity and a lower resistance of a biotutanol-producing microorganism to biobutanol than those of bioethanol. As a result, the international researches focus on the improvement in the productivity and resistance. Under the circumstance, CaTHL modified protein having high functionality of the present invention can be expected to contribute the improved productivity of biobutanol and to be original technology for the research and development, and commercialization of bioenergy.

Furthermore, the present invention provides EcTHL protein having an excellent efficiency of biobutanol compared to conventional wild-type CaTHL protein, so as to considerably contribute the production of biobutanol.

The invention is further explained in more detail with reference to the following examples. These examples, however, should not be interpreted as limiting the scope of the invention in any manner.

Example 1

Preparation of Thiolase Protein

**1.1: Preparation of *Clostridium acetobutylicum* THL (CaTHL) and Modified Protein**

The chromosome of *Clostridium acetobutylicim* was given from the biological resource center of Korean Research Institute of Bioscience & Biotechnology. The CaTHL gene was amplified by PCR using the primer pairs shown in Table 1 at the reaction condition of Table 2. To perform the over-expression of the recombinant protein having Hexa-Histidine tagat C-terminus in *E. coli*, the obtained gene of CaTHL was cloned to the expression vector pET-30a(+) (Invitrogen) by using the restriction enzymes of NdeI and XhoI (New England BioLabs Ins.).

TABLE 1

Primer pairs

| SEQ ID NO | Primer | Sequence |
| --- | --- | --- |
| 5 | CaTHL NdeI Forward | 5'-CGCGCATATGAAAGAAGTTGTAATAGCTAGTGC-3' |
| 6 | CaTHL XhoI Reverse | 5'-CGCGCTCGAGGCACTTTTCTAGCAATATTGCTGTTC-3' |
| 7 | CaTHL V77Q Forward | 5'-CTTTTAAAGCAGGATTACCACAAGAAATTCCAGCTATG-3' |
| 8 | CaTHL V77Q Reverse | 5'-CATAGCTGGAATTTCTTGTGGTAATCCTGCTTTAAAAG-3' |
| 9 | CaTHL P80T(+V77Q) Forward | 5'-GATTACCACAAGAAATTACAGCTATGACTATTAATAAG-3' |
| 10 | CaTHL P80T(+V77Q) Reverse | 5'-CTTATTAATAGTCATAGCTGTAATTTCTTGTGGTAATC-3' |
| 11 | CaTHL N153Y Forward | 5'-GATTGTGGGATGCATTTTATGATTACCACATGG-3' |
| 12 | CaTHL N153Y Reverse | 5'-CCATGTGGTAATCATAAAATGCATCCCACAATC-3' |
| 13 | CaTHL A286K Forward | 5'-CAGGAGTTGACCCAAAAATAATGGGATATGG-3' |
| 14 | CaTHL A286K Reverse | 5'-CCATATCCCATTATTTTGGGTCAACTCCTG-3' |
| 15 | CaTHL Y290T (+A286K) Forward | 5'-CCCAAAAATAATGGGAACTGGACCTTTCTATGC-3' |
| 16 | CaTHL Y290T (+A286K) Reverse | 5'-GCATAGAAAGGTCCAGTTCCCATTATTTTTGGG-3' |

TABLE 2

The PCR condition

| | Temperature | Time | Cycle |
| --- | --- | --- | --- |
| Pre-denature | 95° C. | 5 min. | 1 cycle |
| Denature | 95° C. | 45 sec | 30 cycles |
| Annealing | 56° C. | 45 sec | |
| Elongation | 72° C. | 3 min | |
| Post-elongation | 72° C. | 5 min | 1 cycle | pET-30a(+) cloned with CaTHL gene was transformed into *E. coli* (competent cell) of B834(DE3)/BL21(DE3) strain prepared by Inoue method at 42° C. with heat shock in order to over-express the recombinant protein.

The transformed *E. coli* was cultured at LB medium (Sigma) on a large scale at 37° C. After inoculating the cell at an amount of strain volume 1% (v/v) with respect of the medium volume in a shacking incubator, the over-expression of the recombinant protein was induced by 1 mM IPTG (Isopropyl β-D-1-thiogalactopyranoside) at $O.D_{600}$ 0.5, and then cultured at 22° C. overnight.

The cultured cells were harvested and separated by centrifuging at 2,000 rpm for 10 minutes to remove the supernatant. The cells were re-suspended in a solution of 40 mM Tris-HCl pH8.0/5 mM β-mercaptoethanol (BME) and performed with sonication. The lysed product was centrifuged at 15,000 rpm for 1 hour, and the supernatant was collected to obtain the soluble protein.

The obtained recombinant protein was purified by using the affinity of Hexa-Histidine tag to nickel. Namely, the crude extract (supernatant) was poured to Econo-column (Bio-rad) filled with about 10 ml Ni-NTA resin(QIAGEN) to make the recombinant protein adsorb to Ni-NTA resin, and was flowed with 50 ml of washing buffer including 40 mM Tris-HCl pH8.0/5 mM β mercaptoethanol/27 mM Imidazole to increase the purity of protein. Then, the large amount of recombinant protein was separated and purified by eluting with elution buffer of 40 mM Tris-HCl pH8.0/5 mM β-mercaptoethanol/150 mM Imidazole.

The recombinant protein purified by Ni-NTA was further purified on a large scale according to the size-exclusion chromatography. A solution of 40 mM Tris-HCl pH8.0/5 mM β-mercaptoethanol was eluted to Superdex200 column (Amersham) at a speed of 2.5 ml/min to remove the protein of *E. coli*, and the protein (41.2 kDa) was taken to prepare the CaTHL protein.

The modified protein of CaTHL was prepared by performing site-directed mutagenesis using a primer pair in Table 1.

**1.2: Preparation of *E. coli* THL (EcTHL) Protein**

Protein EcTHL was prepared as similar method to Example 1.1. The chromosome of *Escherichia coli* (K-12) was given from the biological resource center of Korean Research Institute of Bioscience & Biotechnology. The CaTHL gene was amplified by PCR using the primer pairs specific to EcTHL gene (EcTHL_F_BamHI; 5'-CCGGATC- CATGAAAAATTGTGTCATCGTCAGTGC-3' (SEQ ID NO 17), and EcTHL_F_XhoI; 5'-CCCTCGAGTTAAT-TCAACCGTTCAATCACCATCG-3' (SEQ ID NO 18)) at the reaction condition of Table 2.

The amplified gene was cloned to expression vector pPROEXHTb (Invitrogen) with the restriction enzymes of BamHI and XhoI (New England Biolab). The cleavage site of rTEV (recombinant Tobaco Etch Virus) protease (Invitrogen Inc.) which was located at N-terminus of pPROEXHTb, and between the Hexa-Histidine tag and the protein, and Hexa-Histidine tag was removed from the recombinant.

According to the same method of Example 1.1, the expression vector containing EcTHL gene was introduced to *E. coli* to express EcTHL protein on a large scale. According to the same method of Example 1.1, the recombinant protein was recovered by using Ni-NTA column, and then was carried out by treatment of negative purification using rTEV and Ni-NTA column, ion-exchange chromatography, and size-exclusion chromatography sequentially to obtain EcTHL protein (41.3 kDa) with the removal of N-terminal Hexa-Histidine tag at high purity.

Example 2

Identification of Three-Dimensional Structure of CaTHL

The recombinant CaTHL protein purified highly in Example 1.1 was concentrated by using a protein concentration kit VIVASPIN (Sartorious stedim biotech) to be 20 mg/ml, and then crystallized successfully with a Sitting-drop plate (Hampton Research) under the condition of 30% (v/v) PEG (Polyethylene glycol) 400 (Sigma Aldrich)/0.1M Acetate pH4.5/0.1M Calcium Acetate (Sigma Aldrich).

The data on protein crystal were collected by X-ray diffraction method at 6C1 beamline of Pohang Accelerator Laboratory). The data images were managed by indexing and scaling using HKL2000 software (HKL Research, Ins). By using three-dimensional structure of ZrTHL (P07097, Ec number=2.3.1.9) as a template, the electron density map was made via molecular replacement (MR) process. The modeling of three-dimensional structure of protein was carried out by using COOT software on the basis of the electron density map, so as to identify the three-dimensional structure shown FIG. 1.

Two Cysteins at positions 88 and 378 in the active site of the protein form the disulfide bond due to the oxidation that occurs in the contacts with oxygen in air at the processes of purification and crystallization (FIG. 1). However, wild-type CaTHL protein has very unstable 3D structure and forms the disulfide bond even under somewhat oxidative circumstance. The 3D protein structure of FIG. 1 in Example 1 and FIG. 3 in Example 3 showed the results of the protein including Serine substituted at Cystein residue (C88S) of position 88 in wild-type CaTHL.

Example 3

The Structural Stability of CaTHL and EcTHL Protein

The structural stability of CaTHL and EcTHL protein of Examples 1.1 and 1.2 were compared by analyzing the 3D structure of CaTHL (NP_349476, Ec number=2.3.1.9) and EcTHL (ZP_03027833, Ec number=2.3.1.9) under the oxidative condition, according to the same method of Example 2.

The 3D structures of CaTHL (C88S, treated with a reducing agent of 5 mM DTT) and EcTHL (treated with 0.5 mM $H_2O_2$ under the oxidative condition) are shown in FIG. 3. While EcTHL becomes stable due to strong hydrogen bond in the surrounding area, CaTHL protein has no strong hydrogen bond, and is not stable. The stability in surrounding area has competitive relationship with the formation of disulfide bond. That is, the binding force of disulfide bond formed between two Cysteins is very higher than the force stabilizing the surrounding region, and thus, the disulfide bond can be formed. On the other hand, EcTHL protein has very stable structure in the surrounding region. If the binding force of disulfide bond formed between two Cysteins is not sufficient to induce the structural change in the surrounding region, the disulfide bond cannot be formed even under the oxidative circumstance. The present invention identified firstly that the proteins have similar structure and function, the different in the modulation mechanism is caused by the structural stability of protein.

This example proves that CaTHL is controlled by redox-switch modulation due to the non-redox-switch modulation under the oxidative condition.

Example 4

Test for CaTHL Activity Controlled by Redox-Switch Modulation

The activities of protein CaTHL and EcTHL were tested by reacting coenzyme A (CoA) and Acetoacetyl-CoA, and measuring the wavelength at 303 nm for the reduced activity of Acetoacetyl-CoA depending on the process of reaction. To measure the activity of protein, 0.13 mM Acetoacetyl-CoA (MP bio), 0.33 mM CoA (MP bio), and CaTHL 0.015 mg of Example 1.1 or EcTHL 0.015 mg of Example 1.2 were reacted in 100 ml of reaction solution containing 67 mM Tris-HCl/5 mM $MgCl_2$.

In addition, the activity of THL proteins showed the relative number based on that of EcTHL in FIG. 2, when the protein was treated by 1 mM DTT. As shown in FIG. 2, the CaTHL activity which can be controlled by redox-switch modulation has about 30 percent of EcTHL activity with no control of redox-switch modulation. The reason may be the disulfide bond formed between two Cystein residues even under the low level oxidative surroundings.

The activity of CaTHL modified protein (N153Y/A286K, V77Q/N153Y/A286K) prepared in Example 1.1 was measured and shown in FIG. 4 together with wild-type CaTHL and EcTHL protein on the basis of 100% of activity of EcTHL. According to the same method of Example 2 (5 mM DTT), the 3D structure of N153Y/A286K modified protein was identified and represented in FIG. 4. While the modified proteins including Serine substituted at Cystein of 88 position (C88S) was used in Example 2 to see the complete 3D structure, the 153Y/A286K modified protein had a good structural stability and thus could be observed even without the amino acids substitution such as C88S.

As shown in FIG. 4, the activity of CaTHL modified protein was about 2.5 times higher than the wild-type CaTHL protein. In particular, 3D structure of the modified protein of N153Y/A286K where Asparagine at position 153 was substituted with Tyrosine and Alanine at position 286 was substituted with Lysine was identified (3D structure of FIG. 4). In addition, it was proven by evidence that the modified protein of N153Y/A286K did not form the disulfide bond, and the stable hydrogen bond in the surrounding region.

What is claimed is:

1. A method of producing a biobutanol comprising the steps of:
culturing a composition for producing a biobutanol with a carbon source to produce a biobutanol; and
recovering the produced biobutanol,
wherein the composition for producing a biobutanol comprises a *Clostridium acetobutylicum* transformant comprising a polynucleotide encoding a protein having the amino acid sequence of SEQ ID NO: 2 or SEQ ID NO: 3, and
wherein the biobutanol is 1-butanol.

* * * * *